US 6,342,251 B1

(12) United States Patent
Illum et al.

(10) Patent No.: US 6,342,251 B1
(45) Date of Patent: Jan. 29, 2002

(54) COMPOSITIONS FOR NASAL ADMINISTRATION (75) Inventors: Lisbeth Illum; Peter James Watts, both of Nottingham (GB)

(73) Assignee: West Pharmaceutical Services Drug Delivery & Clinical Research Centre Limited, Nottingham (GB)

( * ) Notice: Subject to any disclaimer, the term of this patent is extended or adjusted under 35 U.S.C. 154(b) by 0 days.

(21) Appl. No.: 09/586,139

(22) Filed: Jun. 2, 2000

Related U.S. Application Data (63) Continuation of application No. PCT/GB98/03572, filed on Nov. 27, 1998.

(30) Foreign Application Priority Data

Dec. 2, 1997 (GB) .............................................. 9725519
Mar. 13, 1998 (GB) .............................................. 9805253

(51) Int. Cl.$^7$ ............................ A61K 9/50; A61K 47/30
(52) U.S. Cl. ...................... 424/501; 424/502; 514/772.3
(58) Field of Search ................................ 424/501, 502; 514/772.3

(56) References Cited

U.S. PATENT DOCUMENTS

| 4,826,683 A | 5/1989 | Bates |
| 4,915,948 A | 4/1990 | Gallopo et al. |
| 4,983,385 A | 1/1991 | Hasegawa et al. |
| 5,147,648 A | 9/1992 | Bannert |
| 5,318,780 A | 6/1994 | Viegas et al. |
| 5,456,745 A | 10/1995 | Roreger et al. |
| 5,804,212 A | 9/1998 | Illum |

FOREIGN PATENT DOCUMENTS

| EP | 0 289 512 B1 | 11/1988 |
| EP | 0 306 454 A2 | 3/1989 |
| EP | 0 518 798 A2 | 12/1992 |
| JP | 62-236862 A | 10/1987 |
| WO | WO 88/04926 | 7/1988 |
| WO | WO 94/22445 | 10/1994 |
| WO | WO 9422445 A | * 10/1994 |
| WO | WO 98/47535 | 10/1998 |

OTHER PUBLICATIONS

Aspden, et al., Chitosan as a nasal delivery system: "The Effect of Chitosan Solutions on in Vitro and in Vivo Mucociliary Transport Rates in Human Turbinates and Volunteers," J. Pharm. Sci.86(4): 509–13 (1997).

Axelos & Thibault, "The Chemistry of Low–Methoxyl Pectin Gelatin"in The Chemistry and Technology of Pectin, pp. 109–118, Academic Press: New York, (1991).

Aydin & Akbuga, "Preparation and Evaluation of Pectin Beads," Int. J. Pharm. 137:133–36 (1996).

Brown, et al., "Spreading and Retention of Vaginal Formulations in Post–Menopausal Women as Assessed by Gamma Scintigraphy," Pharm. Res. 14(8): 1073–78 (1997).

Burgalassi, et al., "A Novel Mucoadhesive Buccal Drug Delivery System," Proc. 1$^{st}$World Meet. APGI/APV Budapest, 9/11, pp. 839–840 (1995).

Chetoni, et al., "Veicoli Oftalmici Mucoadhesivi: Studio Preliminare Della Farmacocinctica Oculare 'in vivo'," Boll. Chem. Farm. 135(2): 147–49 (1996).

(List continued on next page.)

Primary Examiner—Carlos A. Azpuru
(74) Attorney, Agent, or Firm—Akin, Gump, Strauss, Hauer & Feld, L.L.P.

(57) ABSTRACT

There is provided a composition for the nasal delivery of a drug suitable for the treatment of erectile dysfunction to a mammal wherein the composition is adapted to provide an initial rise in plasma level followed by a sustained plasma level of the drug.

35 Claims, 4 Drawing Sheets

OTHER PUBLICATIONS

Illum & Fisher, "Intranasal Delivery of Peptides and Proteins" in *Inhalation Delivery of Therapeutic Peptides and Protein*(Adjci & Gupta, eds.), pp. 135–184, Marcel Dekker, Inc.: New York (1997).

Illum, et al., "Chitosan as a Novel Nasal Delivery System for Peptide Drugs," Pharm. Res. 11(8): 1186–89 (1994).

Illum, et al., "Bioadhesive Microspheres as a Potential Nasal Drug Delivery System," Int. J. Pharm. 39:189–99 (1987).

Martindale, *The Extra Pharmacopocia*, 31$^{st}$Ed., The Pharmaceutical Press: London (1996) (copy not included; too voluminous to attach).

Oechslein, et al., "Nasal Delivery of Octreotide: Absorption Enhancement by Particulate Carrier Systems, " Int. J. Pharm. 139:25–32 (1996).

Popovici & Szasz, "Mucoadhesive Gel with Polyuranides for Endonasal Administration" in *Buccal and Nasal Administration as Alternatives to Parental Administration, Minutes of a European Symposium*, (Duchene, ed.), pp. 292–296 Sante: Paris, France (1992).

Potts, et al., "In Vivo Determination of the Oesophageal Retention of Smart Hydrogel," Proceed. Intern. Symp. Dontrol Res. Bioact. Mater. 24:335–36 (1997).

Rolin, et al., "Pectin" in *Industrial Gums 3d*, Academic Press: New York, pp. 257–293 (1993).

Smart, et al., "An In–Vitro Investigation of Mucosa–Adhesive Materials for Use in Controlled Drug Delivery," J. Pharm. Pharmacol., 36: 295–99 (1984).

Walter, "Analytical and Graphical Methods for Pectin" in *The Chemistry and Technology of Pectin*, pp. 189–125, Academic Press: New York (1991).

* cited by examiner

COMPOSITIONS FOR NASAL ADMINISTRATION

CROSS-REFERENCE TO RELATED APPLICATION

This application is a continuation of International application No. PCT/GB98/03572 filed Nov. 27, 1998 the disclosure of which is incorporated herein by reference.

BACKGROUND OF THE INVENTION

This invention relates to compositions for nasal administration of drugs and particularly to compositions for nasal administration of drugs for treating erectile dysfunction, such as apomorphine. The invention also relates to the nasal administration of drugs for treating erectile dysfunction.

Erectile dysfunction is a major medical problem in middle-aged males. A variety of medical treatments has been proposed including local injections as well as hormone therapy. The prostaglandins have been especially useful in this regard.

Other drugs suitable for the treatment of dysfunction include alpha-adrenoreceptor antagonists, e.g. phentolamine, phenoxybenzamine, yohimbine, moxislyte delaquamine; compounds with central $D_2$-receptor antagonist activity, e.g. apomorphine; compounds that act primarily by blocking the re-uptake of serotonin into nerve terminals, e.g. tadone and chlorophenylpiperazine; competitive and selective inhibitors of c-GMP type V phosphodiesterases, e.g. sildenafil; L-arginine; and papaverine.

Presently, administration of the above drugs can often involve the local injection of the penis with attendant problems of compliance. A more discreet, non-invasive method for the treatment of erectile dysfunction would be of considerable advantage.

A drug for erectile dysfunction could be given orally in order to be absorbed from the gastrointestinal tract, but it is well known by those skilled in the art that oral absorption can be slow since the drug has to pass through the stomach into the small intestine to the absorptive regions. The appearance of the drug in the intestine can be delayed by food. Thus, oral absorption tends to be erratic and unpredictable. Hence, this route of delivery is not feasible. The buccal cavity, including the sublingual and buccal tissues, is an alternative site for administration. However, generally speaking drug absorption from this site is slow since the tissues of the mouth are not intended for the efficient uptake of substances, unlike the intestines. Moreover, drugs placed in the mouth can be bitter as well as irritant.

The lungs offer another site for the delivery of drugs. The lungs can provide rapid absorption, but administration needs to be conducted with a device in the form of a nebulizer or inhaler and can be limited by the dose. Many drugs are irritant when blown into the lungs and can cause bronchospasm.

It is known that the nasal epithelium has good permeability and a good blood supply and that drugs that are metabolised after oral administration can be well absorbed from the nose since this route avoids the first-pass metabolic effect in the liver. Hence, the nasal administration of drugs for the treatment of erectile dysfunction is potentially attractive and has been attempted. However, side effects and adverse reactions were common.

It is known that the drug apomorphine (6aR)-5, 6, 6a, 7-tetrahydro-6-methyl-4H-dibenzo(d, e, g) quinoline-10, 11-diol hemihydrate can be effective in the treatment of erectile dysfunction (DanJou et al. Brit. J. Clin. Pharmacol. 26, 733, 1988). However, the drug is better known for its use in disease conditions such as Parkinsonism where oral, rectal and nasal routes have been reported. Intranasal apomorphine has been shown to be useful in Parkinson's disease (Sam et al. Eur. J. Drug Metab. Pharmacokinet. 20, 27, 1995; Dewey et al. Clin. Neuropharmacol. 19, 193, 1996), but is associated with transient nasal blockage and a burning sensation. (Kleedorifer et al, Neurology 41, 761, 1991).

The extent of nasal absorption of apomorphine can be enhanced using various agents such as those described by Merkus that include cyclodextrins (WO-91/22445). The bioavailability, defined as the quantity of drug appearing in the systemic circulation as compared to a control in the form of a subcutaneous injection, is stated to be about 40%.

While local reactions and side effects may be acceptable for a patient receiving nasal apomorphine for the treatment of Parkinson's disease, such side effects would be totally inappropriate for an apparently healthy patient taking nasal apomorphine for the treatment of erectile dysfunction.

Attention has been given to the route of administration of apomorphine for use in erectile dysfunction with an emphasis on convenience. Heaton et al. (Neurology, 45, 200–205) compared different routes of administration in a study conducted in patients. They reported that nasal administration of apomorphine gave rapid onset of action but was associated with unacceptable side effects such as yawning, nausea, vomiting, dizziness, blurred vision, diaphoresis, pallor and mild hypertension and, therefore, was not suitable. Their preferred system was a sublingual formulation as further defined in U.S. Pat No. 5,624,677 and WO-95/28930. However, as discussed above, while sublingual formulations can lead to the absorption of drugs, it is known that such absorption can be slow and variable. Moreover, the quantity absorbed may be limited due to the poor permeability of the oral mucosal membranes in man. In addition, a green colouration of the tongue following sublingual apomorphine has been reported together with poor taste and mucosal ulceration.

Thus, the nasal administration of apomorphine has been described in the prior art literature and in patents. The formulations described were generally simple in nature and all would have led to a pulsatile delivery of the drug resulting in a sharp and high initial peak in the plasma level-time profile leading to local reactions and side effects. In particular, none of the nasal formulations described in the prior art comprised an additive intended to modulate the rapid absorption of the drug.

In WO-94/27576 it is disclosed that the nasal delivery of nicotine could be modified to provide a combination of a peak level (to provide the so-called "buzz" effect of nicotine delivered by a cigarette) and a subsequent controlled release phase. Thus, WO-94/27576 deals with the problem of providing input of nicotine into the bloodstream over a prolonged period of time. The reduction of the plasma level-time profile in order to minimize side effects and adverse reactions for drugs used in the treatment of erectile dysfunction such as apomorphine is neither mentioned nor suggested.

Ugowk et al (J. Control. Rel. 48, 1997, 302) has described mucoadhesive nasal forms for apomorphine hydrochloride for the treatment of Parkinson's disease. An attempt was made to incorporate apomorphine into gelatin microspheres, but the encapsulation efficiencies were reported to be sometimes very low. Moreover, the drug was released rapidly. Ugowk et al also described powder formulations of apomorphine together with polycarbophil or carbomer (carboxypolymethylene) where 100 mg of apomorphine was combined with 1 g of polymer and then freeze dried. The compositions of the present invention were not described.

Thus, the prior art teaches that the nasal delivery of most drugs for the treatment of erectile dysfunction tends to be associated with unacceptable side effects.

Controlled release nasal formulations for the treatment of erectile dysfunction have not been described previously.

As a result of investigations into this problem, the applicant has realised that the adverse reactions and side effects associated with the nasal administration of drugs for treating erectile dysfunction such as apomorphine may be the result of an inappropriate plasma level/time profile and, more specifically, a result of an initial high peak plasma level. We have also realised that such side effects may be reduced and even eliminated by combining the drug with certain pharmaceutical excipients that provide a controlled release effect such as polysaccharides and block copolymers containing ethylene oxide (oxyethylene) moieties. More particularly, we have now discovered controlled release nasal formulations for drugs intended for the treatment of erectile dysfunction that will provide an initial rise in plasma level of the drug followed by a more sustained level of drug input. These nasal formulations can provide a flatter plasma level/time profile after nasal administration by which we mean a reduction in the peak plasma level, but not necessarily a reduction in the area under the plasma level versus time profile.

SUMMARY OF THE INVENTION

According to a first aspect of the present invention there is provided a composition for nasal delivery comprising a drug suitable for the treatment of erectile dysfunction, wherein the composition is adapted to provide an initial rise in plasma level followed by a sustained plasma level of the drug.

According to a second aspect of the present invention there is provided a composition for nasal delivery comprising a drug useful in the treatment of erectile dysfunction, e.g. apomorphine or a salt thereof, and one or more excipients, e.g. in the form of anionic or cationic polysaccharides depending on the drug or block copolymers containing ethylene oxide moieties, wherein the composition is adapted to provide an initial rise in plasma level followed by a sustained plasma level of the drug.

It will be apparent to those skilled in the art that some of the drugs described herein as being useful in the treatment of erectile dysfunction are also known to be useful in the treatment of other conditions and that the compositions of the invention containing such drugs could also be used in the treatment of these other conditions. A particular example is apomorphine for treating Parkinson's disease.

With such compositions it is now possible to administer drugs that are suitable for treating erectile dysfunction through the nasal cavity to give a blood level versus time profile of the drug in the systemic circulation that may provide an effective erection in patients with erectile dysfunction, but without significant adverse reactions and side effects. As discussed above, a simple nasal spray containing such a drug is an unsatisfactory dosage form since it provides a high peak level of the drug in the blood initially followed by a rapid decline in this level leading to adverse reactions and poor efficacy.

When drugs are administered using the nasal formulations of the invention, the initial rise in drug plasma level is rapid, although not as rapid as the rise that results when the same drugs are administered using conventional nasal formulations. Moreover, the peak plasma level of drug attained with the nasal formulations of the invention is not as high as that attained with conventional nasal formulations.

By "initial rise in plasma level of the drug" we mean that the peak plasma level will typically be attained in a time less than 45 minutes, preferably in less than 30 minutes and more preferably in less than 15 minutes after nasal application. The peak in the plasma level concentration versus time profile (e.g. in ng/ml) will typically be reduced to 75% or less, preferably 50% or less of the level obtained with an immediate release formulation of the drug, e.g. as is obtained with conventional nasal spray solutions which are not adapted to provide a controlled release effect.

Each drug will have its own particular range of effective concentration depending upon the properties of the drug. For example, for apomorphine the "initial rise in plasma level" of the drug should be to a level between 0.05 and 50 ng/ml, preferably between 0.25 and 10 ng/ml and more preferably between 0.5 and 5.0 ng/ml in less than 30 minutes, preferably in less than 20 minutes and more preferably in less than 10 minutes after nasal application of the composition.

By a "sustained plasma level" of drug we mean that the plasma level is typically maintained at a level that is necessary for a clinical effect (effective concentration) for between 5 and 120 minutes, preferably between 10 and 60 minutes and more preferably between 15 and 45 minutes.

In a preferred embodiment, the plasma level of drug will remain at approximately the level attained after the initial rise in plasma level for between 5 and 120 min, preferably between 10 and 60 min and more preferably between 15 and 45 min.

The drugs which are used in the compositions of the invention may be weakly basic or weakly acidic. By "a weak base" we mean drugs with a pKa less than 10 and by "a weak acid" we mean drugs with a pKa more than 2.5.

Drugs which are suitable for use in the nasal compositions of the invention include alpha-adrenoreceptor antagonists, e.g. phentolamine, phenoxybenzamine, yohimbine, moxisylyte delaquamine; compounds with central $D_2$-receptor antagonist activity, e.g. apomorphine; compounds that act primarily by blocking the re-uptake of serotonin into nerve terminals, e.g. trazadone and chlorophenylpiperazine; competitive and selective inhibitors of c-GMP type V phosphodiesterases, e.g. sildenafil; L-arginine; and papaverine.

Pharmaceutically acceptable derivatives of the above compounds, such as the pharmaceutically acceptable salts thereof may also be used. A detailed review of these drugs is included in the review entitled Drugs for the Treatment of Impotence by Gascia-Reboll et al. Drugs and Aging 11, 140–151 (1997).

Preferred drugs include those with central $D_2$-receptor antagonist activity or the alpha-adrenoreceptor antagonists. Drugs with central $D_2$-receptor antagonist activity are of particular interest, especially apomorphine.

A variety of pharmaceutically acceptable excipients can be employed in the compositions of the invention including those that form a complex with or entrap the drug. Particular materials include the polysaccharides and PEGylated block copolymers, i.e. block copolymers containing a block made up of repeating ethylene oxide moieties.

Suitable excipients in the case of liquid compositions include natural polymeric materials, such as sodium alginate, xanthan, gellan gum, welan, rhamsan, agar, carageenan, dextran sulphate, keratan, dermatan, pectin, hyaluronic acid and salts thereof. Modified polysaccharide materials such as carboxymethyl cellulose can also be employed as can block copolymers containing one or more blocks made up of repeating ethylene oxide units. These materials are given as examples and the list is not to be taken as exhaustive.

In one method for preparing liquid compositions, the excipient material such as a polysaccharide or a block copolymer containing ethylene oxide moieties is dissolve in ultrapure water or a buffer system or in ultrapure water to which has been added various salts such as sodium chloride. The solution is stirred overnight or until the material has dissolved. With apomorphine, the drug may be dissolved in a similar aqueous system and added to the solution of the excipient material. Alternatively, the apomorphine may be dissolved directly in the excipient solution. A suitable concentration of apomorphine in the final liquid composition is in the range of from 1 mg/ml to 200 mg/ml, preferably in the range of from 2 mg/ml to 100 mg/ml and more preferably in the range of from 5 mg/ml to 50 mg/ml. The concentration of excipient material needed is dependent on the type of material used but is typically between 0.01% w/v and 50% w/v, by which we mean from 0.01 to 50 g of excipient per 100 mls of the liquid, e.g. water. A preferred concentration of the excipient material is in the range 0.1% w/v to 50% w/v, i.e. 0.1 to 50 g of excipient per 100 mls of the liquid, more preferably in the range 0.5% w/v to 50% w/v and particularly in the range 1.0% w/v to 30% w/v.

For powder compositions, it is possible to use carboxylated starch microspheres or positively charged microspheres available from Perstorp (Sweden) and microspheres produced from natural polymers such as carboxylmethyl cellulose, sodium alginate and chitosan.

In one method for preparing powder systems, microspheres having a mean diameter of between 0.5 μm–300 μm are suspended in water or in water containing the dissolved drug and the formulation freeze dried. If the microspheres are suspended in pure water, then the drug is added to this suspension prior to freeze dying. With apomorphine, the final concentration of apomorphine per mg of microsphere is typically between 0.01 mg/mg and 5.0 mg/mg, preferably between 0.02 mg/mg and 2.5 mg/mg and more preferably between 0.025 mg/mg and 0.25 mg/mg. Weight ratios of drug to microspheres in the range of from 1 part drug to 5 to 10 parts of the microspheres are especially preferred.

In another method for preparing powder systems in the form of microspheres, the drug such as apomorphine and the microspheres are mixed mechanically in the dry state.

When drugs other than apomorphine are employed, the above processes and amounts may be modified readily in accordance with techniques well known to those skilled in the art.

It would also be possible to freeze dry a liquid composition for reconstitution before use by the addition of water.

Preferred excipient materials for liquid compositions include pectin, gellan gum, alginate, welan, rhamsan, xanthan and carageenan, particularly pectin, gellan gum, alginate, welan and rhamsan and especially pectin and gellan gum.

Gellan gum is the deacetylated form of the extracellular polysaccharide from Pseudomonas elodae. Native/high-acyl gellan is composed of a linear sequence of tetra-saccharide repeating units containing D-glucuronopyranosyl, D-glucopyranosyl and L-rhamnopyranosyl units and acyl groups.

Alginate is composed of two building blocks of monomeric units namely β-D-mannuronopyranosyl and α-guluronopyranosyl units. The ratio of D-mannuronic acid and L-guluronic acid components and their sequence predetermines the properties observed for alginates extracted from different seaweed sources.

Welan is produced by an Alcaligene species. Welan has the same basic repeating unit as gellan but with a single glycosyl sidechain substituent. The side unit can be either an α-L-rhamnopyranosyl or an α-L-mannopyranosyl unit linked (1–>3) to the 4-0-substituted β-D-glucopyranosyl unit in the backbone.

Rhamsan is produced by an Alcaligenes species. Rhamsan has the same repeating backbone unit as that of gellan but with a disaccharide sidechain on 0–6 of the 3–O-substituted β-D-glucopyranosyl unit. The side chain is a β-D-glucopyranosyl-(1-6)-α-D-glucopyranosyl unit.

Xanthan is produced by a number of Xanthomonas strains. The polymer backbone, made up of (1–>4)-linked βD-glucopyranosyl units is identical to that of cellulose. To alternate D-glucosyl units at the 0–3 position, a trisaccharide side chain containing a D-glucoronosyl unit between two D-mannosyl units is attached. The terminal β-D-mannopyranosyl unit is glycosidically linked to the 0–4 position of the β-D-glucopyranosyluronic acid unit, which in turn is glycosidically linked to the 0–2 position of an α-D-mannopyranosyl unit.

Carageenan is a group of linear galactan polysaccharides extracted from red seaweeds of the Gigartinaceae, Hypneaceae, Solieriaceae, Phyllophoraceae and Furcellariaceae families.

Pectin is an especially preferred material and is obtained from the dilute acid extract of the inner portion of the rind of citrus fruits or from apple pomace. It consists of partially methoxylated polygalacturonic acids. The gelling properties of pectin solutions can be controlled by the concentration of the pectin, the type of pectin, especially the degree of esterification and the presence of added salts.

Mixtures of excipients can also be used, such as mixtures of pectin or gellan with other polymers such as alginate, gelling of the mixture being caused by the pectin or gellan gum. Other combinations of gums can also be used, particularly where the combination gives a synergistic effect, for example in terms of gelation properties. An example is xanthan—locust bean gum combinations.

A preferred excipient for liquid compositions is one that allows the composition to be administered as a mobile liquid but in the nasal cavity will cause the composition to gel, thereby providing a bioadhesive effect which acts to hold the drug at the absorptive surface for an extended period of time. The anionic polysaccharides pectin and gellan are examples of materials which when formulated into a suitable composition will gel in the nasal cavity owing to the presence of cations in the nasal fluids.

The liquid compositions comprising pectin or gellan will typically comprise from 0.01 to 20% w/v of the pectin or gellan in water or an aqueous buffer system, by which we mean that the pectin or gellan will be present in an amount of from 0.01 to 20 g per 100 mls of water or aqueous buffer. A preferred concentration for the pectin or gellan in the water or aqueous buffer is in the range of from 0.1% to 15% w/v, more preferably 0.1 to 5.0% w/v and particularly 0.2% to 1% w/v.

For gelling to occur in the nasal cavity with a liquid composition comprising an excipient which gels in the presence of ions, such as pectin or gellan gum, it is likely to be necessary to add monovalent and/or divalent cations to the composition so that it is close to the point of electrolyte induced gelation. When such a composition is administered to the nasal cavity, the endogenous cations present in the nasal fluids will cause the mobile liquid composition to gel. In other words, the ionic strength of the composition is kept sufficiently low to obtain a low viscosity formulation that is easy to administer, but sufficiently high to ensure gelation once administered into the nasal cavity where gelation will take place due to the presence of cations in the nasal fluids.

Suitable cations for adding to the composition include sodium, potassium, magnesium and calcium. The ionic concentrations are chosen according to the degree of gelling required, and allowing for the effect that ionised drug present may have on gelling since certain drug molecules that are weakly basic and positively charged such as apomoxphine will also act as monovalent cations and will tend to have an effect on the gelling properties of the pectin or gellan system. For example, for a liquid composition comprising 0.2% w/v of gellan, i.e. 0.2 g of gellan per 100 mls of liquid, the divalent ions calcium and magnesium give maximum gel hardness and modulus at molar concentrations approximately one fortieth (¹⁄₄₀) of those required with the monovalent ions sodium and potassium. A finite concentration of each cation is required to induce gelation.

The ionic strength for a liquid nasal composition comprising 0.5% w/v of pectin or gellan gum can be in the range of 0.1 mM–50 mM for monovalent cations with the preferred range being 1 mM–5 mM and in the range of 0.1 mM–5 mM for divalent cations with the preferred range being 0.15 mM to 1 mM. For higher concentrations of pectin or gellan gum the ionic strengths should be lowered accordingly. The cations will compete with a positively charged drug such as apomorphine for binding with the anionic polysaccharide and the concentration of cations should be controlled so that a sufficient amount of positively charged drug will bind with the ion-exchanged anionic polysaccharide.

The complex between a basic drug such as apomorphine and the ion-exchange anionic polysaccharide forms as a result of ionic interaction between the negatively charged polysaccharide and the positively charged drug. The pH of the composition must therefore be such that the two species are well ionised. With apomorphine, the pH should be kept in the range of from pH 3 to pH 8, preferably in the range of from pH 4 to pH 6, by the presence of appropriate buffers or acids. For these ion-exchange polysaccharides, the positively charged drug such as apomorphine can be added either as the base or as a salt. When the drug is used in its salt form it will tend to ionise once in an aqueous environment and if it is in base form the pH of the system can be controlled by the addition of appropriate acids so as to ensure that the drug is ionised and able to interact with the polysaccharide.

Block copolymers such as a poloxamer (polyoxyethylene-polyoxypropylene block copolymer) or a block copolymer of polylactic acid and polyoxyethylene (PLA-PEG) may also be used as the excipient in liquid compositions. The poloxamers can be obtained from BASF as the Pluronic™ and Tetronic™ series with different molecular weights and block structures. A preferred block copolymer is Pluronic™ F127 also known as Poloxamer 407.

Other polymers which may be used as an excipient include PLA-PEG copolymers which can be synthesised by the methods described in EP-A-0166596 or by the methods described by Deng et al (J. Polymer Sci. Part C Polymer letters, 24, 411, 1988), Zhu et al. (J. Polym. Sci. Polm. Chem. 27,2151, 1989) or Gref et al (Science,263, 1600, 1994),PCT/WO95/03357. Water soluble linear tri-block copolymers of PLA-PEG that gel when the temperature is raised are especially preferred. These are described by Jeong et al. Nature. 388, 860, 1997. A suitable concentration of the block copolymer in the liquid formulation is from 5 to 50% w/v, by which we mean from 5 to 50 g of copolymer per 100 mls of the liquid, e.g. water, with a concentration between 10 and 30% w/v being particularly preferred.

The liquid nasal compositions of the invention can also contain any other pharmacologically-acceptable, non-toxic ingredients such as preservatives, antioxidants and flavourings. Benzalkonium chloride may be used as a preservative. It is o known that apomorphine can demonte instability, probably due to auto-oxidation. Thus, stabilising agents such as sodium metabisulphite or ascorbic acid can be included in the compositions.

When the formulations according to the present invention are in the form of microspheres, polysaccharide microspheres may be used including those which carry suitable anionic groups such as carboxylic acid residues, carboxymethyl groups, sulphopropyl groups and methylsulphonate groups or cationic groups such as amino groups. Carboxylated starch microspheres are especially preferred. Carboxylated starch microspheres (Cadexomer™) are available from Perstorp (Sweden).

Other suitable materials for the microspheres include hyaluronic acid, chondroitin sulphate, alginate, heparin and heparin-albumin conjugates, as described in Kwon et al. (Int. J. Pharm. 79, 191, 1991).

Further materials that may be used for the microspheres include carboxymethyl dextran (e.g. CM Sephadex™), sulphopropyl dextran (e.g. SP Sephadex™), carboxymethyl agarose (e.g. CM Sepharose™), carboxymethyl cellulose, cellulose phosphate, sulphoxyethyl cellulose, agarose (e.g. Sepharose™), cellulose beads (e.g. Sephacel ™) and dextran beads (e.g. Sephadex ™) which are all available from Pharmacia, Sweden.

The term microsphere as used herein refers particularly to substantially spherical particles which can be a monolithic solid sphere or a small capsule. To ensure correct deposition in the nasal cavity, the microspheres preferably have a mean diameter of between 0.5 and 250 $\mu$m, preferably between 10 $\mu$m and 150 $\mu$m and more preferably between 10 and 100 $\mu$m as measured using a conventional light microscope.

Microspheres can be made by procedures well known in the art including spray drying, coacervation and emulsification (see for example Davis et al. Microsphere and Drug Therapy, Elsevier, 1984; Benoit et al. Biodegradable Microspheres: Advances in Production Technologies, Chapter 3, Ed. Benita, S, Dekker, New York, 1996; Microencapsulation and related Drug Processes, Ed. Deasy, Dekker, 1984, New York, pp 82, 181 and 225; U.S. Pat. No. 2,730,457 and U.S. Pat. No. 3,663,687).

In the spray drying process, the material used to form the body of the microsphere is dissolved in a suitable solvent (usually water) and the solution spray dried by passing it through an atomisation nozzle into a heated chamber. The solvent evaporates to leave solid particles in the form of microspheres.

In the process of coacervation, microspheres can be produced by interacting a solution of a polysaccharide carrying a positive charge with a solution of a polysaccharide carrying a negative charge. The polysaccharides interact to form an insoluble coupling that can be recovered as microspheres.

In the emulsification process, an aqueous solution of the polysaccharide is dispersed in an oil phase to produce a water in oil emulsion in which the polysaccharide solution is in the form of discrete droplets dispersed in oil. The microspheres can be formed by heating, chilling or cross-linking the polysaccharide and recovered by dissolving the oil in a suitable solvent.

The microspheres can be hardened before combining with the drug by well known cross-inking procedures such as heat treatment or by using chemical cross-linking agents. Suitable agents include dialdehydes, including glyoxal, malondialdehyde, succinicaldehyde, adipaldehyde, glutaraldehyde and phthalaldehyde, diketones such as butadione, epichlorohydrin, polyphosphate and borate. Dialdehydes are used to cross-link proteins such as albumin by interaction with amino groups and diketones form Schiff bases with amino groups. Epichlorohydrin converts compounds with nucleophilic centres such as amino or hydroxyl to epoxide derivatives. The cross-linkers used for ion-exchange microspheres should not be directed towards the negatively or alternatively positively charged groups required for binding the drug.

For microsphere compositions of the invention, the drug such as apomorphine is preferably in salt form to ensure that it is ionised. The drug is sorbed to the microspheres by admixing with the microspheres after their formation. This may be achieved by suspending the microspheres in an aqueous buffer and then adding the drug in solution. The microspheres can then be recovered by a process of freeze drying.

The drug can be combined with the microspheres at different ratios. A quantity of microspheres greater than that of the drug on a weight to weight basis is preferred. The amount chosen will be dictated by the dose of the drug and the complexation properties of the microsphere.

It is possible to control the shape of the plasma level time profile by the amount of anionic or cationic polysaccharide material or polymer that is added to the nasal formulation containing the drug useful in erectile dysfunction. Taking apomorphine as the drug, a plasma level suitable for the treatment of erectile dysfunction is believed to be from 0.5 to 5.0 ng/ml. The duration of effect should be from 15 to 30 minutes. A suitable nasal dose of apomorphine will be between 0.5 and 5.0 mg. A preferred nasal dose will be between 1.0 and 3.0 mg.

The formulation, if in the form of a liquid, can be administered using a simple nasal spray device available from companies such as Valois or Pfeiffer.

Microspheres or other powder formulations can be administered using a powder device. Suitable powder devices are available from Bespak in the United Kingdom. Other suitable powder devices are the nasal insufflators used for drugs such as Rhinocort™ (marketed by Teijin in Japan). The device from Direct Haler (Denrmark) can also be used. Such nasal devices can be passive with the patient having to draw a dose of the powder into the nasal cavity from the device through their own inspiration or active with powder being blown into the nasal cavity through some mechanical process, e.g. using a rubber bulb or spring system.

BRIEF DESCRIPTION OF THE SEVERAL VIEWS OF THE DRAWINGS

Those skilled in the art will also appreciate that many of the currently available devices for the administration of dry powders to the lung can easily be adapted to deliver the powder formulations of this invention to the nose. Suitable devices include those available from Dura, Valois, Glaxo-Wellcome, Norton, Fisons, Leiras (RPR). These devices are well described in the prior art and are known by names such as Ultrahaler™, Prohaler™ and Easi-breathe™. The dry powder devices intended for lung delivery can be modified by the attachment of a small nozzle. The device from Orion in Finland is available with such a nasal nozzle system.

In the drawings:

FIG. 1 is a schematic drawing of a Franz diffusion cell.

FIG. 2 is a graph showing the release of apomorphine from liquid formulations prepared from Pectin and Pluronic™ F127 and from a simple apomorphine solution as control.

FIG. 3 is a graph showing the plasma level versus time profile expected for a liquid apomorphine formulation comprising a gelling polysaccharide excipient following nasal administration to a rat.

FIG. 4 is a graph showing the plasma level versus time profile expected for a liquid apomorphine formulation comprising a block copolymer excipient following nasal administration to a rat.

DETAILED DESCRIPTION OF THE INVENTION

The present invention is now illustrated but not limited with reference to the following examples.

The following examples provide details of the preparation and release properties of nasal formulations useful for the delivery of drugs intended for the treatment of erectile dysfunction such as apomorphine. The release of the drug was measured using a diffision cell apparatus based on an original design by Franz. Such Franz diffusion cells for measuring drug release are familiar to the skilled person and are described in WO-94/27576. The diffusion of the drug across an artificial membrane in the form of cellulose nitrate into an electrolyte solution chosen to simulate the ionic environment of the nasal cavity was conducted at 37° C. A diagram of the apparatus is provided in FIG. 1.

The electrolyte fluid had the following composition:

$Na^+$ions—150 mEq/1

$K^+$ions—40 mEq/1, $Ca^{2+}$ions—8 mEq/1

A 2 mg/ml aqueous solution of apomorphine was used as a control. 20 mg of apomorphine were weighed into a 10 ml volumetric flask and the flask contents made up to volume with water.

In each experiment a 50 μl aliquot of the formulation was applied to the membrane in order to measure diffusion across the membrane.

EXAMPLE 1

Pectin Based Formulation

Into a 25 ml volumetric flask was weighed 250 mg of pectin 110 (obtained from Copenhagen Pectin A/S). 15 ml of ultrapure water was then added and the solution stirred overnight on a magnetic stirrer. The flask contents were made up to volume with ultrapure water.

10 mg of apomorphine (obtained from Sigma) were weighed into a 5 ml volumetric flask. To the flask was added 3 ml of the 10 mg/ml pectin 110 solution. The mixture was stired for 30 minutes and the flask contents made to volume with the 10 mg/ml pectin 110 solution.

EXAMPLE 2

Pluronic™ F127 Formulation

Pluronic™ F127 (Poloxamer 407) was obtained from BASF. Into a 100 ml conical flask was weighed 10 g of Pluronic™ F127. 50 ml of ultrapure water was then added and the solution left to stir on a magnetic stirrer. The conical flask was sealed with parafilm and was placed in the refrigerator at 5° C. for 30 minutes. This ensures that the Pluronic™ F127 solution is in the liquid state since solutions of this block copolymer are known to gel when the temperature is raised.

10 mg of apomorphine were weighed into a 5 ml volumetric flask. To the flask was added 3 ml of the cooled, 200 mg/ml Pluronic™ F127 solution. The mixture was allowed to stir and the flask contents made to volume with the 200 mg/ml Pluronic™ F127 solution.

EXAMPLE 3

Measurement of Drug Release Kinetics

The Franz diffusion cell apparatus was used to measure diffusion of drug across an artificial cellulose nitrate membrane (0.45 μm thickness) from the following formulations:

I. 2 mg/ml apomorphine (control solution)

II. 2 mg/ml apomorphine/10 mg/ml pectin 110

III. 2 mg/ml apomorphine/200 mg/ml Pluronic™ F127

In each case a 50 μl aliquot of formulation was applied to the membrane in order to measure diffusion of drug across the membrane. The Pluronic™ F127 formulation had to be cooled for at least 30 minutes at 5° C. to keep the formulation in the liquid state.

Figure 1:
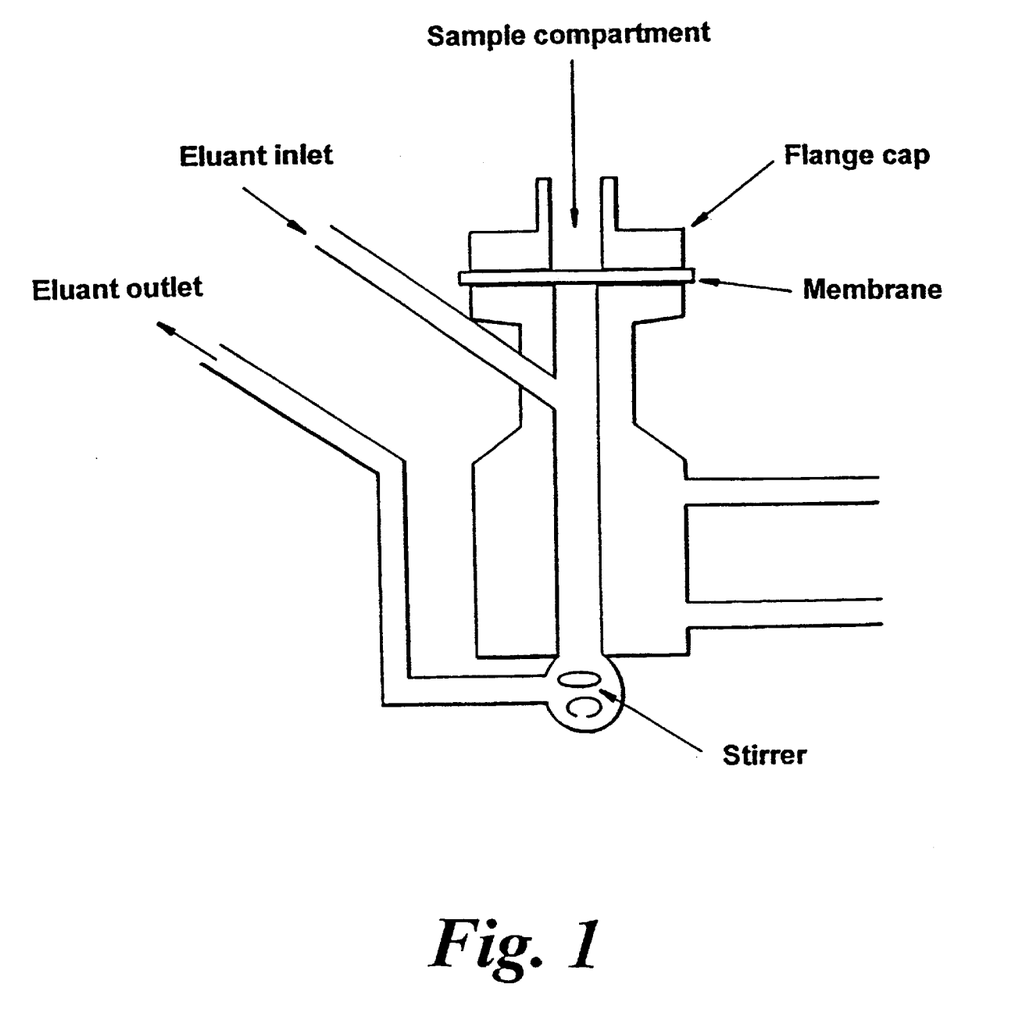
Figure 2:
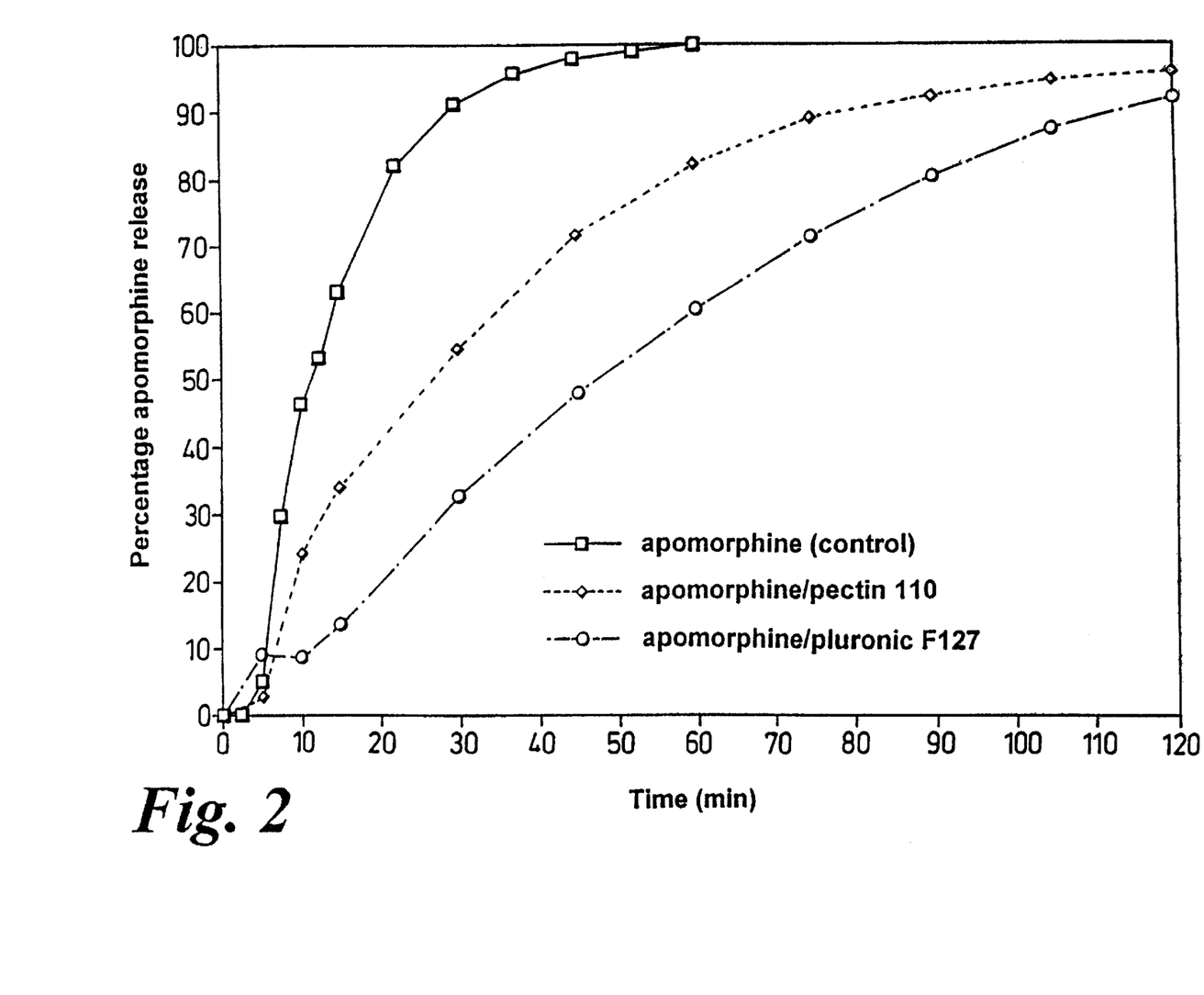

For each of the formulations I to III, two Franz diffusion cell release profiles were obtained, the data absorbance vs time were meaned, expressed as a percentage and plotted. The results are illustrated in FIG. 2.

The control solution of apomorphine alone diffused rapidly through the cellulose nitrate membrane with 100% of the drug entering the Franz diffusion cell in 60 minutes. In contrast, approximately 60% of the apomorphine was released from the pectin 110 system and approximately 80% of the apomorphine was released from the Pluronic™ ™ F127 after 60 minutes. After 120 minutes, 96% and 92% of the apomorphine was released from the pectin 110 and Pluronic™ F127 systems respectively.

EXAMPLE 4

A Microsphere Based Formulation

Starch microspheres carrying carboxyl groups (Cadexomer™) were obtained from Perstorp Fine Chemical Companies, Sweden. The microspheres had a particle diameter in the range of 53–106 micron in the unswollen state. 5 g of a 10:1 weight ratio of carboxylated to non-carboxylated starch microspheres were mixed with 20 mls of an aqueous solution of apomorphine (pH adjusted to 7) at a concentration of 5% w/v (i.e. 5 g of apomorphine per 100 mls of solution). The system was freeze dried and 50 mg doses of the powder were packed into gelatin capsules for administration by a nasal insufflator device.

EXAMPLE 5

Preparation of Apomorphine Polymer Complex

An apomorphine/gellan complex was prepared as follows.

A gellan solution was prepared by adding 500 mg of gellan to 15 ml of water. The resulting mixture was stirred overnight on a magnetic stirrer to dissolve the gellan in the water. The solution was then made up to 25 ml with water. An aqueous solution of apomorphine 10 mg/ml was added to the gellan solution. A cloudy mixture resulted. This was stirred and the precipitate allowed to settle. e slurry was centrifuged and the recovered precipitate washed with deionized water to remove excess drug. The precipitate was recovered once again by centrifugation and freeze dried in a 100 ml round bottom flask at −60° C. for 24 hours.

A fluffy material was produced. This can be placed in suspension in a suitable vehicle such as saline and then dosed intranasally as a spray. The material can also be dosed as a powder by physical admixture with adhesive microspheres such as starch microspheres as described in PCT/GB88/00836.

EXAMPLE 6

Pharmacokinetic Evaluation

The beneficial properties of the formulations that comprise this invention can be evaluated in a suitable animal model such as the rat in order to determine the changed pharmacokinetic profile of the drug as compared to a simple nasal solution.

Anaesthetised male Sprague-Dawley rats (body weight 250 g to 330 g) can be used in such experiments. The rats are starved for 12 hours prior to dosing. Anaesthesia is induced by interitoneal administration of urethane (1.25 g/kg of either a 10% w/v or 40% w tv solution) and maintained by additional doses of 1 mL of a 40% w/v solution as required.

The animals are modified surgically so as to maintain respiratory function and to prevent the nasal formulation reaching the gastrointestinal tract.

Blood samples are obtained by cannulation of the jugular vein. This method has been described in detail by Hirai (Int J. Pharn. 1, 317, 1981) and modified by Fisher et al. (J. Pharm. Pharmacol. 39, 357, 1987). The formulations are dosed into the nasal cavity in a volume of 50 μl. Blood samples are collected at suitable time intervals in order to obtain a pharmacokinetic profile (e.g. 0, 2, 4, 6, 8, 10, 15, 20, 45, 60, 90, 120 mins post administration).

The blood samples are assayed for drug by standard HPLC. For apomorphine, the method is based on HPLC with electrochemical detection as described by Sam et al. (J. Chromat. of B. 658, 311, 1994). A dose of 0.5 mg of apomorphine is used for liquid polysaccharide and microsphere formulations. This dose is chosen in order to obtain sufficient concentration for analysis. For liquid formulations based on gelling block copolymers a dose of 1 mg of apomorphine is used. When employing a simple solution form of apomorphine a sharp peak in the plasma level profile is found. However, for the polysaccharide based systems in solution, suspension or microsphere form a delayed peak of about 30 minutes is found. The peak height is substantially reduced (for example from 1400 ng/ml for the simple nasal solution to 350 ng/ml for the polysaccharide liquid system described in Example 1.

For the poloxamer vehicle a similar delay in the peak height is found and a delay in the time to maximum from less than 10 minutes to greater than 30 minutes. The plasma concentration is reduced from about 1500 ng/ml for a simple nasal solution to about 750 ng/ml for the Poloxamer 407 (Pluronic™ F-127 system) described in Example 2.

Figure 3:
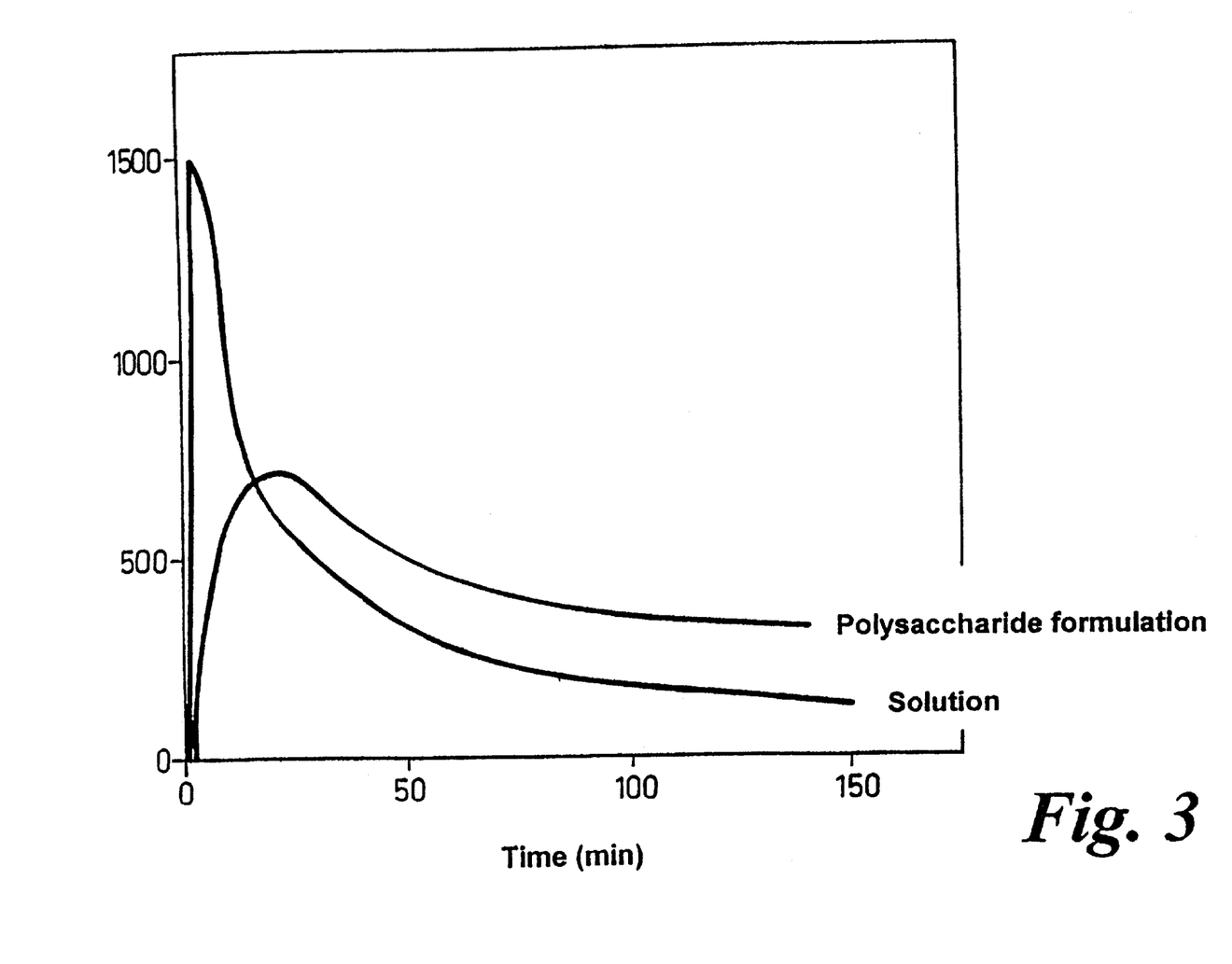
Figure 4:
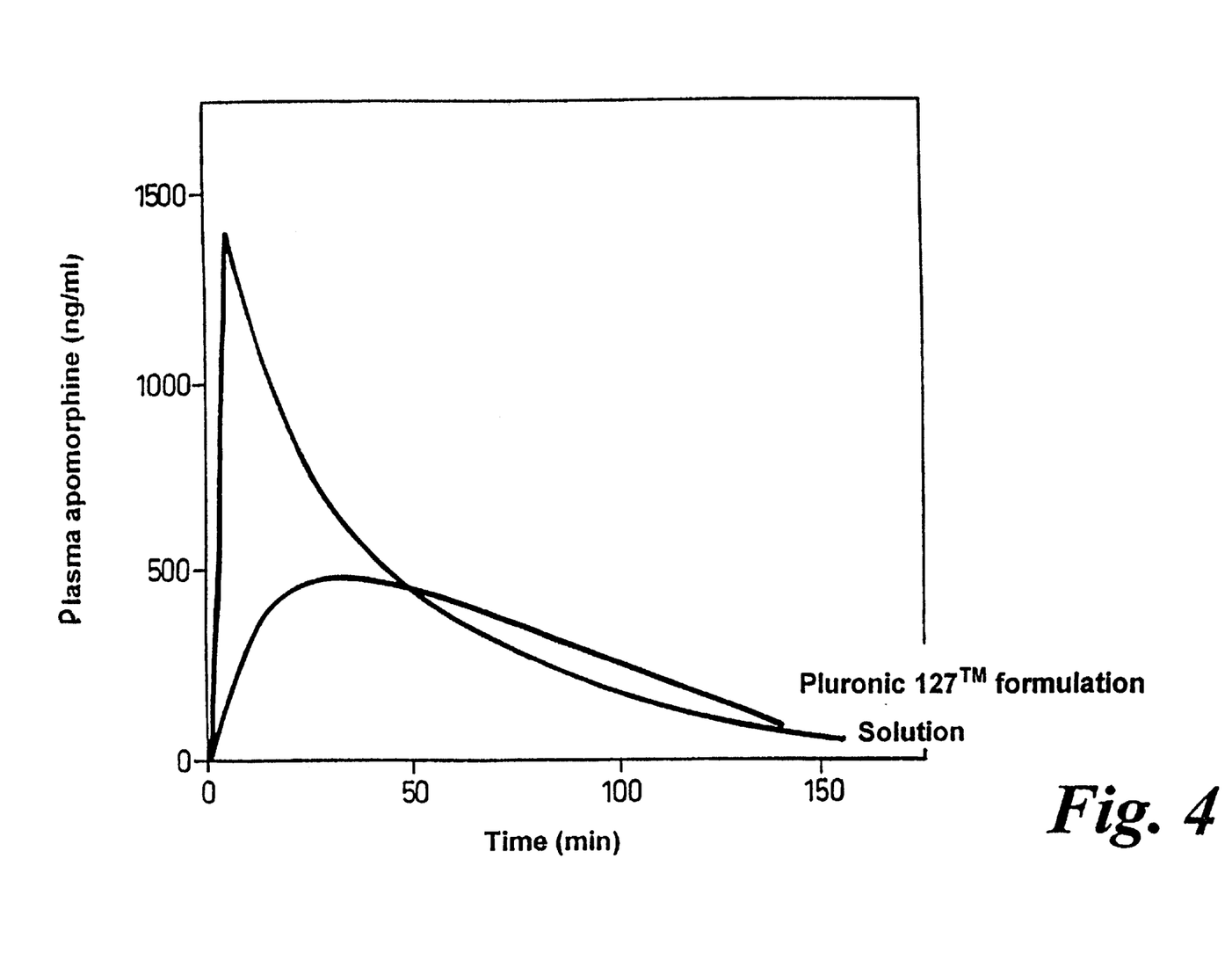

Representative curves are shown in FIGS. 3 and 4.

It will be clear to the skilled artisan that the formulations described in the foregoing examples can be further modified for ease of administration by the addition of other known pharmaceutical excipients. Also other drugs useful in the treatment of erectile dysfunction can be used in place of the apomorphine.

We claim:

1. A composition for nasal delivery comprising a drug suitable for the treatment of erectile dysfunction and one or more excipients, wherein;
   1) the composition is either a liquid or a powder;
   2) at least one or more excipients selected from the group consisting of block copolymers comprising repeating ethylene oxide moieties, anionic polysaccharides and ion exchange polymeric materials; and
   3) the composition is adapted to provide an initial rise in plasma level followed by a sustained plasma level of the drug.

2. A composition according to claim 1, wherein the drug is a weak base or a weak acid and the combination of drug with excipient results in complexation as a result of an ion exchange process.

3. A composition according to claim 1, wherein the drug is a weak base or a weak acid, and is combined with a block copolymer.

4. A composition according to claim 3, wherein the block copolymer is selected from the group consisting of poloxamines, poloxamers and polylactide-polyoxyethylene copolymers.

5. A composition according to claim 1, wherein the excipient is an ion exchange polymeric material.

6. A composition according to claim 1, wherein the excipient provides for controlled delivery of the drug to the nasal membrane and comprises a polysaccharide and/or block copolymer comprising a polyoxyethylene block.

7. A composition according to claim 1, wherein the excipient is an anionic polysaccharide selected from the group consisting of xanthans, gellans, alginates, hyaluronic acid, and carboxymethylcelluse.

8. A composition according to claim 1, wherein the excipient is a pectin.

9. A composition according to claim 1, wherein the excipient is a carboxylated starch.

10. A composition according to claim 1, wherein the excipient is chitosan.

11. A composition according to claim 1, wherein the composition is a liquid.

12. A composition according to claim 1, wherein the composition is a liquid system which is adapted to gel in the nasal cavity.

13. A composition according to claim 12, wherein the composition is adapted to gel on contact with the cations present in the nasal cavity.

14. A composition according to claim 13, wherein the composition comprises a source of cations.

15. A composition according to claim 13, wherein the excipient comprises pectin and/or gellan.

16. A composition according to claim 1, wherein the composition is in the form of microspheres.

17. A composition according to claim 16, wherein the microspheres are produced from carboxylated starch.

18. A composition according to claim 16, wherein the microspheres are produced from chitosan.

19. A composition according to claim 1, wherein the composition comprises a drug selected from the group consisting of alpha-adrenoreceptor antagonists, compounds with central $D_2$-receptor antagonist activity, compounds that act primarily by blocking the re-uptake of serotonin into nerve terminals, competitive and selective inhibitors of c-GMP type V phosphodiesterases, and pharmaceutically acceptable salts thereof.

20. A composition according to claim 19, wherein the composition comprises a drug with central $D_2$-receptor antagonist activity.

21. A composition according to claim 20, wherein the composition comprises apomorphine.

22. A method for the controlled delivery of a drug to the systemic circulation of a mammal which comprises the nasal administration of a composition according to claim 1, to the mammal.

23. A method of treatment of a disease in which the controlled delivery of a drug to the circulation is desirable which comprises the nasal administration of a composition according to claim 1, to a mammal.

24. A method as claimed in claim 23, wherein the drug is apomorphine and the disease is Parkinson's disease.

25. A method as claimed in claim 23, wherein the disease is erectile dysfunction.

26. A method for treating a disease which comprises nasal administration of a composition according to claim 1.

27. A method for treating erectile dysfunction which comprises nasal administration of a composition according to claim 1.

28. The use of a composition according to claim 1, in the manufacture of a medicament for the controlled delivery of a drug useful in the treatment of erectile dysfunction to the systemic circulation of a mammal.

29. The use of a composition according to claim 1, in the manufacture of a medicament for nasal administration of a drug useful in the treatment of erectile dysfunction.

30. The use of a composition according to claim 1, in the manufacture of a medicament for treatment erectile dysfunction.

31. A process for the preparation of a composition according to claim 1, which comprises admixing the drug with the excipient.

32. A composition according to claim 1, wherein the drug is apomorphine.

33. A composition according to claim 19, wherein the drug is the alpha-adrenoreceptor antagonist which is selected from the group consisting of phentolamine, phenoxybenzamine, yohimbine and moxislyte delaquamine and pharmaceutically acceptable salts thereof.

34. A composition according to claim 19, wherein the drug is a compound that acts primarily by blocking the re-uptake of serotonin into nerve terminals, and the compound is selected from trazadone, chlorophenylpiperazine and pharmaceutically acceptable salts thereof.

35. A composition according to claim 19, wherein the drug is a competitive and selective inhibitor of c-GMP type V phosphodiesterases and is selected from sildenafil, L-arginine, papaverine and pharmaceutically acceptable salts thereof.

* * * * *